(12) United States Patent
Li et al.

(10) Patent No.: US 11,317,800 B2
(45) Date of Patent: May 3, 2022

(54) METHOD OF MONITORING EYE STRAIN AND RELATED OPTICAL SYSTEM

(71) Applicant: Ganzin Technology, Inc., Taipei (TW)

(72) Inventors: Kuei-An Li, New Taipei (TW); Su-Ling Yeh, Taipei (TW); Shao-Yi Chien, Taipei (TW)

(73) Assignee: Ganzin Technology, Inc., Taipei (TW)

( * ) Notice: Subject to any disclaimer, the term of this patent is extended or adjusted under 35 U.S.C. 154(b) by 441 days.

(21) Appl. No.: 16/566,894

(22) Filed: Sep. 11, 2019

(65) Prior Publication Data
US 2020/0205657 A1 Jul. 2, 2020

Related U.S. Application Data

(60) Provisional application No. 62/787,389, filed on Jan. 2, 2019.

(30) Foreign Application Priority Data
Jul. 19, 2019 (TW) .................................. 108125520

(51) Int. Cl.
*A61B 3/113* (2006.01)
*A61B 3/00* (2006.01)

(52) U.S. Cl.
CPC ............. *A61B 3/113* (2013.01); *A61B 3/0025* (2013.01); *A61B 2562/02* (2013.01)

(58) Field of Classification Search
CPC ... A61B 3/113; A61B 3/0025; A61B 2562/02; A61B 5/1103; A61B 3/10; A61B 3/112; A61B 5/0059; A61B 5/746; G06F 2203/011; G06F 3/013; A61H 5/00
USPC ....................................................... 351/209
See application file for complete search history.

(56) References Cited

U.S. PATENT DOCUMENTS

| 2017/0075419 | A1* | 3/2017 | Parthasarathy | G06F 3/013 |
| 2018/0088666 | A1* | 3/2018 | Ayoub | G06V 40/19 |
| 2020/0089316 | A1* | 3/2020 | Raskar | G06F 3/017 |

FOREIGN PATENT DOCUMENTS

| CN | 102357052 A | 2/2012 |
| CN | 204839441 U | 12/2015 |
| CN | 103680465 B | 6/2016 |
| TW | 201828897 A | 8/2018 |
| WO | 2017/001319 A1 | 1/2017 |

* cited by examiner

*Primary Examiner* — Mohammed A Hasan
(74) *Attorney, Agent, or Firm* — Winston Hsu

(57) ABSTRACT

A method of monitoring eye strain includes detecting the blink status, the vergence status and the pupil status of a user, and then determining whether the user encounters eye strain according to at least one of the blink status, the vergence status and the pupil status of the user. The method further includes facilitating the user to blink or informing the user of eye strain.

20 Claims, 2 Drawing Sheets

METHOD OF MONITORING EYE STRAIN AND RELATED OPTICAL SYSTEM

CROSS REFERENCE TO RELATED APPLICATIONS

This application claims priority of U.S. provisional Application No. 62/787,389 filed on Jan. 2, 2019 and Taiwan Application No. 108125520 filed on Jul. 19, 2019.

BACKGROUND OF THE INVENTION

1. Field of the Invention

The present invention is related to a method of monitoring eye strain and related optical system, and more particularly, to a method of monitoring eye strain based on the eye-blink status, the vergence status and the pupil status of user's eyes and related optical system.

2. Description of the Prior Art

Digital device usage has increased substantially in recent years across all age groups, so that extensive daily use for both social and professional purposes is now normal. Prolonged computer, tablet, e-reader and cell phone use without regular screen breaks or proper luminescence causes digital eye strain, also known as computer vision syndrome, which encompasses a range of ocular and visual symptoms. Ocular discomfort due to digital eye strain includes dry eyes, photophobia, blurry vision, body fatigue, headache or lack of concentration.

Virtual reality (VR) is an interactive computer-generated experience taking place within a simulated environment, that incorporates mainly auditory and visual, but also other types of sensory feedback like haptic. VR technologies provide a user wearing special display equipment with an immersive environment similar to the real world and allow the user to interact with a VR object or other users. In normal binocular vision, our eyes naturally adjust their focus to look at something far off or nearby. In a rendered VR world, our eyes are asked to continually adjust their focus even though everything is on a screen only a few inches away, which causes a disruption of our vergence technically known as a vergence-accommodation conflict. Therefore, extended experiences in such immersive virtual environment cause digital eye strain more easily.

SUMMARY OF THE INVENTION

The present invention provides a method of monitoring eye strain. The method includes monitoring a blink status, a vergence status and a pupil status of a user; and determining whether the user encounters an eye strain according to at least one of the blink status, the vergence status and the pupil status of the user.

The present invention also provides an optical system which monitors eye strain. The optical system includes an eye strain detecting module configured to monitor a blink status, a vergence status and a pupil status of a user; and an eye strain analyzing module configured to determine whether the user encounters an eye strain according to at least one of the blink status, the vergence status and the pupil status of the user.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
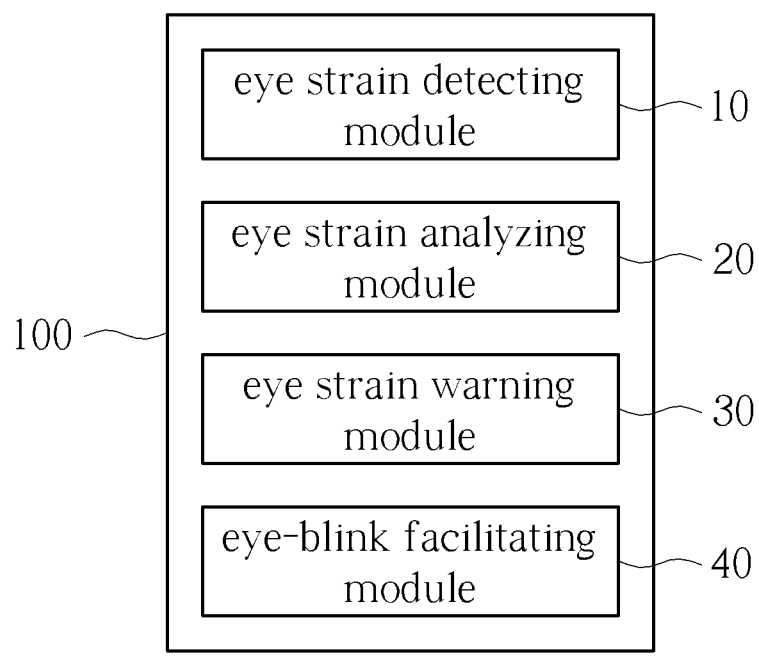
FIG. 1 is a functional diagram of an optical system according to an embodiment of the present invention.

FIG. 1 is a functional diagram of an optical system 100 according to an embodiment of the present invention. The optical system 100 includes an eye strain detecting module 10, an eye strain analyzing module 20, an eye strain warning module 30, and an eye-blink facilitating module 40. The eye strain detecting module 10 is configured to detect the eye-blink status, the vergence status and the pupil status of a user of the optical system 100. The eye strain analyzing module 20 is configured to determine whether the user encounters eye strain according to the ocular information provided by the eye strain detecting module 10. When it is determined that the user encounters eye strain, the eye strain warning module 30 is configured to send a warning message, or the eye-blink facilitating module 40 may be configured to alleviate the eye strain.

Figure 2:
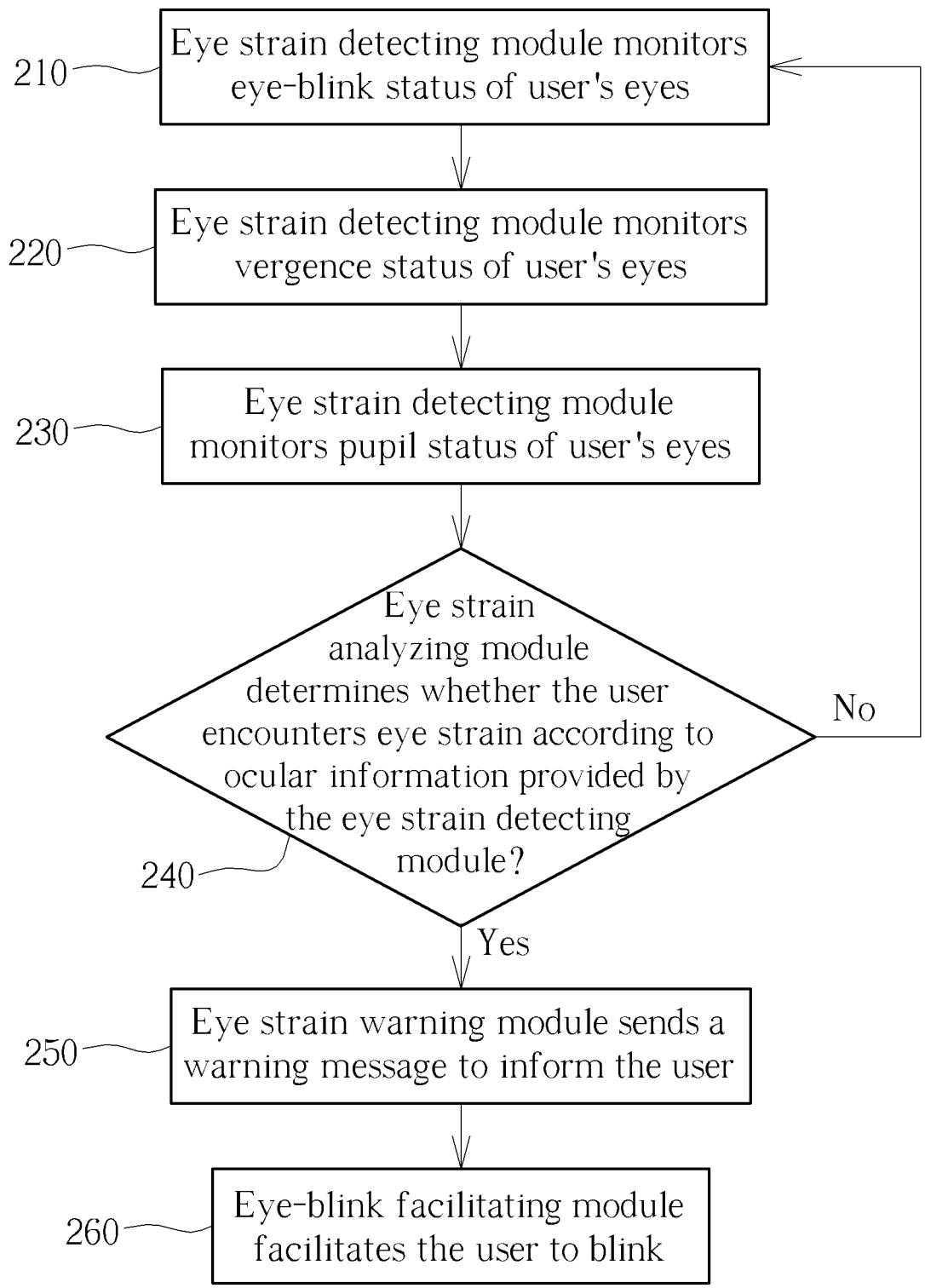
FIG. 2 is a flowchart illustrating the operation of the optical system according to an embodiment of the present invention.

FIG. 2 is a flowchart illustrating the operation of the optical system 100 according to an embodiment of the present invention. The flowchart in FIG. 2 includes the following steps:

Step 210: the eye strain detecting module 10 monitors the eye-blink status of the user's eyes.

Step 220: the eye strain detecting module 10 monitors the vergence status of the user's eyes.

Step 230: the eye strain detecting module 10 monitors the pupil status of the user's eyes.

Step 240: the eye strain analyzing module 20 determines whether the user encounters eye strain according to the ocular information provided by the eye strain detecting module 10; if yes, execute step 250; if no, execute step 210.

Step 250: the eye strain warning module 30 sends a warning message to inform the user.

Step 260: the eye-blink facilitating module 40 facilitates the user to blink.

There are three types of eye blink: reflex blink, spontaneous blink and voluntary blink. A reflex blink is triggered by an external stimulus, such as contact with the cornea, glare or objects that appear rapidly in front of the eyes. A spontaneous blink occurs in the pre-motor brain stem and happens without conscious effort or external stimuli. A voluntary blink is a conscious action for a specific reason. Among them, spontaneous blink and voluntary blink can provide indices of eye strain. The process of eye blinking may be characterized by total lid-contact time, wherein a complete blink occurs when the upper eyelid is in contact with the lower eyelid, and an incomplete blink occurs when the upper eyelid is not in contact with the lower eyelid. A complete blink helps spread tears across and remove irritants from the surface of the cornea and conjunctiva, as well as helps alleviate eye strain by temporarily isolating the eyes from the environment. However, an incomplete blink can result in less pumping activity of the lower eyelid meibomian glands, which eventually causes dry cornea or blocked meibomian glands. Since blinking is often related to cognitive processes, long-time reading, writing or using electronic devices is commonly accompanied by reduced blink rate or reduced completeness, thereby causing ocular discomfort or blurry vision. Also, a voluntary blink involves a stronger forceful closing of the eyelid than a reflex blink, and can trigger more lacrimal gland secretion which better alleviates eye strain.

In this regard, the eye strain detecting module 10 in the optical system 100 is configured to monitor the eye-blink status of the user's eyes in step 210, such as by detecting the spontaneous eye blink rate (SEBR), the inter-eye blink interval (IEBI), the blink duration, the blink amplitude and the blink completeness. These parameters may be used by the eye strain analyzing module 20 for determining whether the user encounters eye strain in step 240. The evaluation of the eye-blink status of the user's eyes may be based on the following conditions: whether the SEBR of the user's eyes is smaller than a predetermined value, whether the IEBI of the user's eyes is longer than a predetermined value, whether the blink duration is shorter than a predetermined period, whether the number of voluntary blink (judged by the blink amplitude) is smaller than a predetermined value, or whether the number of complete blink is smaller than a predetermined value. For example, if at least one of the above-mentioned conditions is satisfied, the eye strain analyzing module 20 determines that the user encounters eye strain.

In the eye structure, the extraocular muscles are the six muscles that control movement of the eye and one muscle that controls eyelid elevation. When a creature with binocular vision looks at an object, the eyes rotate around a horizontal axis so that the projection of the image is in the center of the retina in both eyes. Such simultaneous movement of both eyes in opposite directions to obtain or maintain single binocular vision is called "vergence". Frequent vergence movements bring burden to the extraocular muscles and thus easily induce eye strain. On the other hand, staring at an object for a long time (no vergence movement) results in stiff extraocular muscles and thus also causes ocular discomfort.

Fixation disparity (FD), a parameter for evaluating the accuracy of vergence, is a failure of the two visual axes to simultaneously intersect the object of regard during attempted binocular fixation. More specifically, when looking at an object, fixation disparity prevents the eyes from binocularly aligned at the fovea which provides the clearest vision. The existence of fixation disparity indicates an esophoria (Eso disparity) or an exophoria (Exo disparity) during attempted binocular fixation. The degree of fixation disparity is also associated environmental glare. Mild fixation disparity may be perceptually fused without causing diplopia, but severe fixation disparity may induce or aggravate eye strain. Meanwhile, when a person encounters eye strain, the variation of fixation disparity during a unit time also increases.

In this regard, the eye strain detecting module 10 of the optical system 100 is configured to monitor the vergence status of the user's eyes, such as by detecting the degree and variation of fixation disparity. These parameters may be used by the eye strain analyzing module 20 for determining whether the user encounters eye strain in step 240. For example, if the user has been having a high fixation disparity at least for a predetermined period of time, and/or the variation of fixation disparity remains greater than a predetermined value at least for a predetermined period of time, the eye strain analyzing module 20 determines that the user encounters eye strain.

The iris sphincter muscle is a thin and circular structure in human eyes for controlling the diameter and size of the pupil and thus the amount of light reaching the retina. In response to bright light or focusing on a near object, the iris sphincter muscle constricts the pupil in order to prevent strongly diverging light rays from hitting the periphery of the cornea. Also, in the accommodation reflex when focusing on a near object, the lens becomes thicker, thereby allowing the light rays to refract (bend) more strongly. After extended period of conducting vergence effort tasks, pupillary response tends to slow down. That is, it takes longer for the pupil constriction or dilation to occur in response to an external stimulus for a person with astenopia.

Pupillary hippus is spasmodic, rhythmic, but regular dilating and contracting pupillary movements between the sphincter and dilator muscles. The occurrence of pupillary hippus also increases after extended period of conducting vergence effort tasks, especially for people with astenopia.

In this regard, the eye strain detecting module 10 in the optical system 100 is configured to monitor the pupil status of the user's eyes in step 230, such as by detecting the pupil size, the pupil response time, or the frequency of pupil oscillation. These parameters may be used by the eye strain analyzing module 20 for determining whether the user encounters eye strain in step 240. For example, if the pupil size of the user remains smaller than a predetermined value at least for a predetermined period of time, the pupil response time is not smaller than a predetermined value, and/or the frequency of pupil oscillation is larger than a predetermined value, the eye strain analyzing module 20 determines that the user encounters eye strain.

In an embodiment, the eye strain detecting module 10 includes an optical pupil-based eye-tracker, an Infrared oculography eye-tracker, and an Infrared ocular thermal imager, or a bio-signal sensor. However, the implementation of the eye strain detecting module 10 does not limit the scope of the present invention.

In step 240, the eye strain analyzing module 20 is configured to determine whether the user encounters eye strain according to the ocular information provided by the eye strain detecting module 10. In an embodiment, the eye strain analyzing module 20 may determine whether the user encounters eye strain according to at least one of the eye-blink status, the vergence status and the pupil status of the user's eyes. In another embodiment, the eye strain analyzing module 20 may determine whether the user encounters eye strain according to all of the eye-blink status, the vergence status and the pupil status of the user's eyes.

After it is determined that the user encounters eye strain, the eye strain warning module 30 may send the warning message to inform the user in step 250. In an embodiment, the warning message may be a video image, an audio message, a vibration message, or an olfactory message. However, the method of sending the warning message does not limit the scope of the present invention.

After it is determined that the user encounters eye strain, the eye-blink facilitating module 40 may facilitate the user to blink for alleviating eye strain. In an embodiment, the eye-blink facilitating module 40 includes an air-injecting device capable of puffing a small burst of air into the canthus of human eyes for facilitating eye-blinking, similar to a tonometry test. In another embodiment, the eye-blink facilitating module 40 may emit unperceivable light to stimulate the optical sensors in the retina of human eyes, thereby increasing the number of reflex blink. However, the implementation of the eye-blink facilitating module 40 does not limit the scope of the present invention.

In the optical system 100 of the present invention, the eye strain detecting module 10 can monitor the eye-blink status, the vergence status and the pupil status of the user's eyes. Next, the eye strain analyzing module 20 can determine whether the user encounters eye strain according to the ocular information provided by the eye strain detecting module 10. When it is determined that the user encounters eye strain, the eye strain warning module 30 can remind the user of taking a break, and the eye-blink facilitating module 40 can further facilitate the user to blink for alleviating eye strain.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of monitoring eye strain, comprising:
   monitoring a vergence status and a pupil status of a user;
   monitoring a blink status of the user by detecting at least one of a spontaneous eye blink rate (SEBR), an inter-eye blink interval (IEBI), a blink duration, a blink amplitude and a blink completeness of the user;
   determining whether the user encounters an eye strain according to at least one of the blink status, the vergence status and the pupil status of the user;
   determining whether the SEBR is smaller than a first value, whether the IEBI is longer than a second value, whether the blink duration is shorter than a third value, whether a number of a voluntary blink judged by the blink amplitude is smaller than a fourth value, or whether a number of a complete blink is smaller than a fifth value; and
   determining that the user encounters the eye strain when the SEBR is smaller than the first value, the IEBI is longer than the second value, the blink duration is shorter than the third value, the number of the voluntary blink judged by the blink amplitude is smaller than the fourth value, or the number of the complete blink is smaller than the fifth value.

2. The method of claim 1, wherein monitoring the vergence status includes detecting at least one of a degree of a fixation disparity and a variation of the fixation disparity of the user.

3. The method of claim 2, further comprising:
   determining whether the user has been having a high fixation disparity at least for a first period of time, or the variation of the fixation disparity remains greater than a sixth value at least for a second period of time; and
   determining that the user encounters the eye strain when the user has been having the high fixation disparity at least for the first period of time, or the variation of the fixation disparity remains greater than the sixth value at least for the second period of time.

4. The method of claim 1, wherein monitoring the pupil status includes detecting at least one of a pupil size, a pupil reaction time and a frequency of pupil oscillation of the user.

5. The method of claim 4, further comprising:
   determining whether the pupil size remains smaller than a seventh value at least for a third period of time, the pupil response time is not smaller than an eighth value, or the frequency of pupil oscillation is larger than a ninth value; and
   determining that the user encounters the eye strain when the pupil size remains smaller than the seventh value at least for the third period of time, the pupil response time is not smaller than the eighth value, or the frequency of pupil oscillation is larger than the ninth value.

6. The method of claim 1, further comprising:
   facilitating the user to blink or sending a warning message when determining that the user encounters the eye strain.

7. The method of claim 6, wherein facilitating the user to blink includes puffing gas onto eyes of the user or stimulating optical sensors in the eyes of the user.

8. The method of claim 6, wherein the warning message includes a video message, an audio message, a vibration message, or an olfactory message.

9. An optical system which monitors eye strain, comprising:
   an eye strain detecting module configured to:
      monitor a vergence status and a pupil status of a user; and
      monitor a blink status of the user by detecting at least one of a spontaneous eye blink rate (SEBR), an inter-eye blink interval (IEBI), a blink duration, a blink amplitude and a blink completeness of the user; and
   an eye strain analyzing module configured to:
      determine whether the user encounters an eye strain according to at least one of the blink status, the vergence status and the pupil status of the user;
      determine whether the SEBR is smaller than a first value, whether the IEBI is longer than a second value, whether the blink duration is shorter than a third value, whether a number of a voluntary blink judged by the blink amplitude is smaller than a fourth value, or whether a number of a complete blink is smaller than a fifth value; and
      determine that the user encounters the eye strain when the SEBR is smaller than the first value, the IEBI is longer than the second value, the blink duration is shorter than the third value, the number of the voluntary blink judged by the blink amplitude is smaller than the fourth value, or the number of the complete blink is smaller than the fifth value.

10. The optical system of claim 9, wherein the eye strain detecting module is configured to monitor the vergence status by detecting at least one of a degree of a fixation disparity and a variation of the fixation disparity of the user.

11. The optical system of claim 10, wherein the eye strain analyzing module is further configured to:
   determine whether the user has been having a high fixation disparity at least for a first period of time, or the variation of the fixation disparity remains greater than a sixth value at least for a second period of time; and
   determine that the user encounters the eye strain when the user has been having the high fixation disparity at least for the first period of time, or the variation of the fixation disparity remains greater than the sixth value at least for the second period of time.

12. The optical system of claim 9, wherein the eye strain detecting module is configured to monitor the pupil status by detecting at least one of a pupil size, a pupil reaction time and a frequency of pupil oscillation of the user.

13. The optical system of claim 12, wherein the eye strain analyzing module is further configured to:
   determine whether the pupil size remains smaller than a seventh value at least for a third period of time, the pupil response time is not smaller than an eighth value, or the frequency of pupil oscillation is larger than a ninth value; and determine that the user encounters the eye strain when the pupil size remains smaller than the seventh value at least for the third period of time, the pupil response time is not smaller than the eighth value, or the frequency of pupil oscillation is larger than the ninth value.

14. The optical system of claim 9, further comprising:
an eye-blink facilitating module configured to facilitate the user to blink when the eye strain analyzing module determines that the user encounters the eye strain.

15. The optical system of claim 9, further comprising:
an eye strain warning module configured to send a warning message when the eye strain analyzing module determines that the user encounters the eye strain.

16. The optical system of claim 9, wherein the eye strain warning module includes an optical pupil-based eye-tracker, an Infrared oculography eye-tracker, an Infrared eye thermal imager, or a bio-signal sensor.

17. A method of monitoring eye strain, comprising:
monitoring a blink status and a pupil status of a user;
monitoring a vergence status of the user by detecting at least one of a degree of a fixation disparity and a variation of the fixation disparity of the user;
determining whether the user encounters an eye strain according to at least one of the blink status, the vergence status and the pupil status of the user;
determining whether the user has been having a high fixation disparity at least for a first period of time, or the variation of the fixation disparity remains greater than a predetermined value at least for a second period of time; and
determining that the user encounters the eye strain when the user has been having the high fixation disparity at least for the first period of time, or the variation of the fixation disparity remains greater than the predetermined value at least for the second period of time.

18. A method of monitoring eye strain, comprising:
monitoring a blink status and a vergence status of a user;
monitoring a pupil status of the user by detecting at least one of a pupil size, a pupil reaction time and a frequency of pupil oscillation of the user;
determining whether the user encounters an eye strain according to at least one of the blink status, the vergence status and the pupil status of the user;
determining whether the pupil size remains smaller than a first value at least for a predetermined period of time, the pupil response time is not smaller than a second value, or the frequency of pupil oscillation is larger than a third value; and
determining that the user encounters the eye strain when the pupil size remains smaller than the first value at least for the predetermined period of time, the pupil response time is not smaller than the second value, or the frequency of pupil oscillation is larger than the third value.

19. An optical system which monitors eye strain, comprising:
an eye strain detecting module configured to:
monitor a blink status and a pupil status of a user; and
monitor a vergence status of the user by detecting at least one of a degree of a fixation disparity and a variation of the fixation disparity of the user; and
an eye strain analyzing module configured to:
determine whether the user encounters an eye strain according to at least one of the blink status, the vergence status and the pupil status of the user;
determine whether the user has been having a high fixation disparity at least for a first period of time, or the variation of the fixation disparity remains greater than a predetermined value at least for a second period of time; and
determine that the user encounters the eye strain when the user has been having the high fixation disparity at least for the first period of time, or the variation of the fixation disparity remains greater than the predetermined value at least for the second period of time.

20. An optical system which monitors eye strain, comprising:
an eye strain detecting module configured to:
monitor a blink status and a vergence status of a user; and
monitor a pupil status of the user by detecting at least one of a pupil size, a pupil reaction time and a frequency of pupil oscillation of the user; and
an eye strain analyzing module configured to:
determine whether the user encounters an eye strain according to at least one of the blink status, the vergence status and the pupil status of the user;
determine whether the pupil size remains smaller than a first value at least for a predetermined period of time, the pupil response time is not smaller than a second value, or the frequency of pupil oscillation is larger than a third value; and
determine that the user encounters the eye strain when the pupil size remains smaller than the first value at least for the predetermined period of time, the pupil response time is not smaller than the second value, or the frequency of pupil oscillation is larger than the third value.

* * * * *